(12) United States Patent  
Abbruscato

(10) Patent No.: US 7,115,102 B2
(45) Date of Patent: Oct. 3, 2006

(54) ELECTRONIC STETHOSCOPE SYSTEM

(76) Inventor: Charles R. Abbruscato, 7640 Golden Triangle Dr., Eden Prairie, MN (US) 55344

( * ) Notice: Subject to any disclaimer, the term of this patent is extended or adjusted under 35 U.S.C. 154(b) by 452 days.

(21) Appl. No.: 10/714,373

(22) Filed: Nov. 17, 2003

(65) Prior Publication Data
US 2005/0107715 A1   May 19, 2005

(51) Int. Cl.
A61B 7/00 (2006.01)
(52) U.S. Cl. .................. 600/586; 600/514; 128/904
(58) Field of Classification Search ............... 600/514, 600/586; 128/904; 381/67
See application file for complete search history.

(56) References Cited

U.S. PATENT DOCUMENTS

| | | | |
|---|---|---|---|
| 4,528,690 A * | 7/1985 | Sedgwick | 381/67 |
| 4,731,849 A | 3/1988 | Bloomfield | |
| 4,878,501 A | 11/1989 | Shue | |
| 5,010,890 A | 4/1991 | Pfohl | |
| 5,027,825 A | 7/1991 | Phelps | |
| 5,467,775 A | 11/1995 | Callahan | |
| 5,550,902 A * | 8/1996 | Abbruscato | 379/106.02 |
| 5,557,681 A | 9/1996 | Thomasson | |
| 5,602,924 A | 2/1997 | Durand et al. | |
| 5,604,811 A | 2/1997 | McIntyre | |
| 5,701,904 A | 12/1997 | Simmons | |
| 5,825,895 A | 10/1998 | Grasfield | |
| 5,841,846 A | 11/1998 | Abbruscato | |
| 5,852,263 A | 12/1998 | Dieken | |
| 5,909,495 A | 6/1999 | Andrea | |
| 6,002,777 A | 12/1999 | Grasfield | |
| 6,340,350 B1 | 1/2002 | Simms | |
| 6,533,736 B1 | 3/2003 | Moore | |
| 6,540,673 B1 | 4/2003 | Gopinathan | |
| 6,544,198 B1 | 4/2003 | Chong et al. | |
| 2002/0085724 A1 | 7/2002 | Grasfield et al. | |
| 2003/0002685 A1 | 1/2003 | Werblud | |
| 2003/0072457 A1 | 4/2003 | Grasfield et al. | |

* cited by examiner

Primary Examiner—Robert E. Pezzuto
Assistant Examiner—Tammie K. Heller
(74) Attorney, Agent, or Firm—Miller Patent Services; Jerry A. Miller

(57) ABSTRACT

In a local stethoscope unit, acoustic auscultation sounds picked up by the stethoscope chest piece assembly of a local stethoscope unit are converted to analog electrical signals and then converted to digital signals. The digital signals are conveyed to a data communications system, having data communications device and a data communication channel. The digital signals are transmitted over the digital communications system to a remote stethoscope receiving unit. The remote stethoscope unit converts the digital signals back to the original analog signals suitable for listening.

26 Claims, 2 Drawing Sheets

ELECTRONIC STETHOSCOPE SYSTEM

BACKGROUND OF THE INVENTION

1. Field of the Invention

The present invention relates stethoscopes and in particular to coding and digitally transmitting auscultation sounds to a remote location where the signals are decoded and converted back to analog sounds for listening.

2. Description of Related Art

When a clinician examines a patient, the clinician typically will check the patient's vital signs. Key among the vital signs typically checked are the cardiovascular (heart) and respiratory (lung) sounds of the patient. Sounds coming from the body are referred to as auscultation sounds and a stethoscope is the medical device used to listen to a patient's auscultation sounds. A typical stethoscope will have a bell and diaphragm capability, where the bell position slightly enhances the lower frequency sounds of the beating heart and the diaphragm position is better at passing the higher frequencies, such as the breath sounds of the lungs.

The clinician will place the chest piece of the stethoscope to various spots on the patient's front and back depending on which organ is being monitored. The clinician will also use the bell/diaphragm capability as appropriate to enhance the auscultation exam. While a clinician may wish to see the patient and where the chest piece is being placed, it is not essential that the clinician hold the chest piece. That is, someone else, including the patient can position and hold the chest piece following the instructions of the clinician. As long as there is a video/audio (or at least an audio) connection between the clinician and patient and a data communications channel to pass auscultation sounds, the physician and patient don't have to be physically in the same location. The ability to perform certain medical functions on a patient at a remote location is generally referred to as telemedicine. Having a remote telephonic stethoscope system is essential in performing medical tests that require auscultation in telemedicine.

The output of a typical amplifying stethoscope can be digitized and send over a digital communications channel to a receiving stethoscope unit that converts the digitized signal back to analog to allow a clinician to listen to the sounds. The techniques and equipment available in the prior art to accomplish this produce a digital signal with a data rate that significantly limits the frequency range of the auscultation signal that may be passed over normal telephone lines; hence, many systems are thus restricted to usage between facilities that have broadband communications channels. Currently, most homes do not have broadband communications service. However, nearly all homes have basic telephone service so a remote telephonic stethoscope system that uses a bit rate low enough to be used over a normal telephone line is highly advantageous. Some remote telephonic stethoscope system can accomplish this in a store-and-forward method that approaches real-time operation. That is, they store a brief period of auscultation sounds and then pause in the monitoring of new sounds while they send the stored sounds. This is not real-time and is awkward for the clinician and patient.

Typical remote telephonic stethoscope systems use a relatively large bandwidth, generally in the range of 32 Kb/s to 64 Kb/s. The best state-of-the-art system achieves a modest auscultation bandwidth using 9.6 Kb/s, uses special techniques for error handling and achieves a bandwidth of 30 Hz to 500 Hz.

The prior art includes a remote telephonic stethoscope system that uses Pulse Code Modulation (PCM) and Adaptive Differential PCM (ADPCM) coding and a repeated byte error handling circuit to achieve a low bit rate that passes part of the key auscultation frequency band of interest and operates in real-time, as shown in U.S. Pat. No. 5,841,846. The commercial implementation of this patent also includes in the remote stethoscope unit a monitor port so that the local physician with the patient can listen as well as the remote physician.

The conversion of an analog auscultation signal to a digital auscultation signal (A/D conversion) involves sampling the analog signal periodically and quantizing the samples. How often the analog signal is sampled is dependent on the highest frequency component that is to be passed. According to the Nyquist criteria, it is necessary to sample an analog signal at least twice as often as the highest frequency to be transmitted. For example, to pass a signal up to 3,400 Hz (cycles per second) requires sampling at least 6,800 times a second. While an analog signal is continuous, its digital counterpart is not. Matching the analog sample to its nearest digital equivalent is called quantization. Linear coding typically requires 10–12 bits for each sample and is the easiest and least efficient. PCM provides better efficiency and achieves similar quality with only 8 bits per sample by using a technique called companding where greater sensitivity is given to low volume sounds by assigning relatively more digital values than for high volume sounds. Because the typical signals are band limited in some way, the amplitude difference between two adjacent samples is much smaller than the total possible amplitude range. More sophisticated schemes take advantage of that and produce even greater bandwidth efficiency. Adaptive Differential PCM (ADPCM) yields nearly the same quality as PCM but produces only four bits per sample.

Adaptive delta modulation (ADM), although a known coding scheme, has not been used an electronic stethoscope system. ADM is a sophisticated digital coding method that uses an adaptive differential quantization technique based on the differences between three or four adjacent samples, but only produces one bit for each quantization computation. By looking at multiple samples, both the rate of change as well as the change in amplitude and slope can be used in the computation. Since each computation produces only one bit, rather than four, eight or twelve, there is no need for any synchronization or framing patterns; it is inherently self-synchronizing. A specific implementation of ADM called continuously variable slope delta (CVSD) modulation is used in communications networks where efficiency and robustness against noise is needed.

ADM/CVSD integrated circuits (IC) have been designed for the telephony communications industry. They are tailored for the telephony voice frequency range of 300 Hz to 3,400 Hz and typically include at the encoding side an input filter, an A/D converter and ADM/CVSD algorithm processing and at the decoding side ADM/CVSD algorithm processing, D/A conversion and output filtering.

SUMMARY OF THE INVENTION

The present invention is directed to a stethoscope system, which includes a local stethoscope unit with a chest piece assembly to generate a first analog auscultation signal and a local transmitting section to receive the first analog auscultation signal. The local transmitting section has a first low frequency boost circuit coupled to the chest piece assembly and capable of amplifying a portion of the first analog auscultation signal having frequencies lower than a predetermined frequency level to generate a boosted segment signal and a local encoder coupled to the chest piece assembly and to the first low frequency boost circuit and responsive to the first analog auscultation signal and the boosted segment signal to generate a compressed digital auscultation signal. The stethoscope system further includes a remote stethoscope unit having a remote receiving section and a remote headset, the remote receiving section being coupled to the local encoder and being responsive to the digital auscultation signal to generate a second analog auscultation signal for the remote headset.

The present invention also is directed to a stethoscope system comprising a local stethoscope unit including a local transmitting section and a local receiving section, with the local stethoscope unit having a local transmit mode and a local receive mode; and a remote stethoscope unit including a remote transmitting section and a remote receiving section, with the remote stethoscope unit having a remote transmit mode and a remote receive mode. The stethoscope system further comprises a chest piece assembly detachably coupled to the local transmitting section to generate an analog auscultation signal. The local stethoscope unit is configured to operate in the local transmit mode and the remote stethoscope unit is configured to operate in the remote receive mode in response the chest piece assembly being coupled to the local transmitting section and not coupled the remote transmitting section. The local transmitting section in the transmit mode is coupled to the remote receiving section and the chest piece assembly and is responsive to the analog auscultation signal to generate and transmit a digital auscultation signal to the remote receiving section. The remote receiving section in the receive mode is responsive to the transmitted digital auscultation signal to regenerate the analog auscultation signal. A remote headset receives the regenerated analog auscultation signal.

One novel feature of one embodiment of the present invention is the use in the stethoscope units of a low frequency boost to improve the low frequency response down to approximately 20 Hz. The low frequency boost may be implemented in different ways, such as: 1) in a transmitting section of the local stethoscope unit only (non-switchable), 2) in the transmitting section of the local stethoscope (non-switchable) and the receiving sections of the stethoscope units (switchable with a bell/diaphragm toggle switch), and 3) in the transmitting section of the local stethoscope (switchable) and the receiving sections of the stethoscope units (switchable with the bell/diaphragm toggle switch), where a reverse data channel provides the communications path for the bell/diaphragm switch command from the remote stethoscope unit to the local stethoscope unit. Hence, the present invention provides for boosted, very low auscultation frequency performance bandwidth and for enhanced the bell-diaphragm characteristics of a traditional stethoscope.

Another novel feature of one embodiment of the present invention is that the same stethoscope unit may be used as the local stethoscope unit and remote stethoscope unit. When the chest piece assembly is plugged into the local stethoscope unit, its presence is sensed and the local stethoscope unit automatically goes into its transmit mode. In transmit mode, the auscultation signal is sent by the local stethoscope unit over the data communications channel to the remote stethoscope so that a clinician at the remote stethoscope unit may hear the auscultation sounds. The absence of the chest piece assembly being plugged into the remote stethoscope unit causes the remote stethoscope unit to go into its receive mode to receive the auscultation signal from the data communications channel.

Another novel feature of one embodiment of the present invention is that it provides an efficient, low cost remote telephonic stethoscope system using an ADM/CVSD codec that passes high quality sound using a low bit rate for real-time use over a normal, bandwidth-limited telephone line, while having expanded high auscultation frequency coverage. In other words, the same low bit rate of 9.6 Kb/s of the prior art design is achieved, but this embodiment also achieves a greater frequency bandwidth for the auscultation signal.

Another novel feature of one embodiment of the present invention is to utilize an ADM/CVSD codec IC having a switched capacitor filter to suit the specific needs of a remote telephonic stethoscope system by taking advantage of peculiarities of the codec IC designs and the remote telephonic stethoscope system needs. For example, the clock to a switched capacitor filter in the codec IC with a pass band of 300 Hz to 3,400 Hz may be scaled down, such as by a factor of five, and then the filter has a reduced pass band of 60 Hz to 667 Hz, which is suitable for accommodating the analog auscultation signal.

Another novel feature of one embodiment of the present invention is that the stethoscope units include a data communications interface to the data communications channel which may be optionally synchronous or asynchronous. The data communications interface may allow for a wide variety of data communications systems to be used, including but not limited to IP Networks, modems, data multiplexers, cable extenders, wireless and direct cable connections.

Another novel feature of the one embodiment of the present invention is that a single clock frequency with appropriate dividers leading to each component of the stethoscope units may be used to drive both the ADM/CVSD and USART ICs so that the 7.68 Kb/s data rate is perfectly in synchronization with the 9.6 Kb/s data line rate. This eliminates the possibility of long term data over-runs or under-runs, thereby making the design of the remote stethoscope unit simpler.

BRIEF DESCRIPTION OF THE DRAWINGS

A more complete appreciation of the present invention and many of the attendant advantages thereof will be readily obtained as the same becomes better understood by reference to the following detailed description when considered in connection with the accompanying drawings, wherein.

DETAILED DESCRIPTION OF AN ILLUSTRATIVE EMBODIMENT

In the following description, for purposes of explanation, numerous details are set forth in order to provide a thorough understanding of the disclosed embodiments of the present invention. However, it will be apparent to one skilled in the art that these specific details are not required in order to practice the disclosed embodiments of the present invention. In other instances, well-known electrical structures and circuits are shown in block diagram form in order not to obscure the disclosed embodiments of the present invention.

Figure 1:
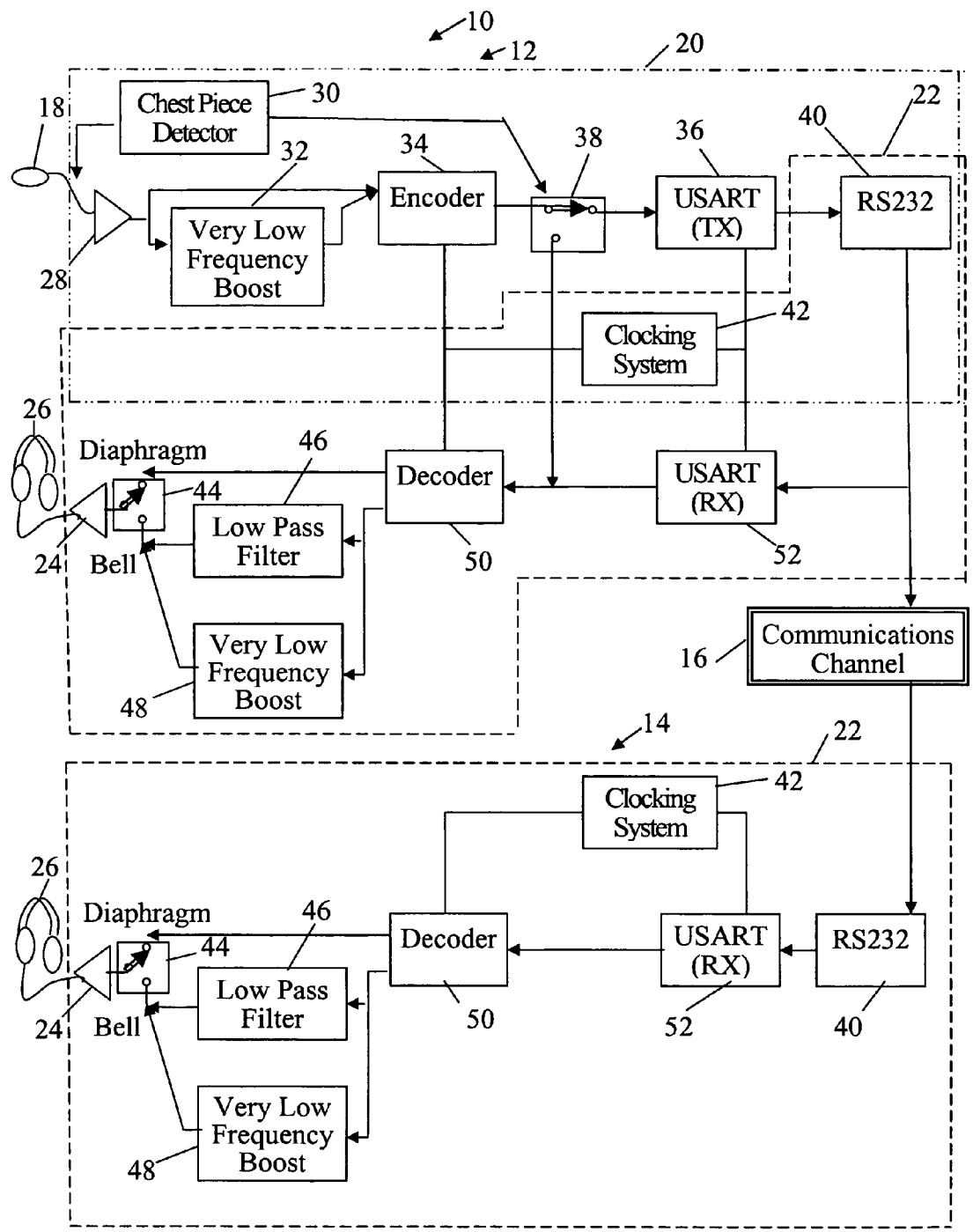
FIG. 1 is a block diagram of the stethoscope system according to one embodiment of the present invention.

With reference to FIG. 1, a stethoscope system 10 is illustrated in one embodiment of the present invention. The stethoscope system 10 includes a local stethoscope unit 12 at a patient's location and a remote stethoscope unit 14 at a clinician's location connected over a data communications channel 16. In the preferred embodiment, the local stethoscope unit 12 and remote stethoscope unit 14 are identical in design, with the exception that a chest piece assembly 18 is needed with the local stethoscope unit 12. The local stethoscope unit 12 includes a local transmitting section 20 and a local receiving section 22. The remote stethoscope unit 14 includes a remote transmitting section (not depicted) and a remote receiving section 22. Since the components of the local stethoscope unit 12 and remote stethoscope unit 14 are identical, they will be given the same reference numbers and will only be described once. To assist in the description of the operation of the a stethoscope system 10, a given component in the local stethoscope unit 12 is described as being "local", whereas the same component in the remote stethoscope unit 14 is described as being "remote", even though the two identical components are identified by the same reference number. In accordance with this practice, the local stethoscope unit 12 includes a local headset driver 24 and local headset 26 and the remote stethoscope unit 14 includes a remote headset driver 24 and a remote headset 26, with the two headsets and two headset drivers being identical. The local stethoscope unit 12 and the remote stethoscope unit 14 each have a transmit mode and a receive mode, with the selected mode determining which sections (i.e. transmitting and receiving sections) are enabled and how they are used, as will be described hereinafter.

The transmitting section 20 of the local stethoscope unit 12 and the transmitting section (not depicted) of the remote stethoscope unit 14 includes an amplifier 28, a chest piece detector 30, a first low frequency boost circuit 32, an encoder 34, a loop-back control 38, a transmitting part 36 of a USART (Universal Synchronous Asynchronous Receiver Transmitter), a RS232 data communications interface 40, and a clocking system 42. The receiving sections 22 of the local and remote stethoscope units 12 and 14 include a bell/diaphragm toggle switch 44, a low pass filter 46, a second low frequency boost circuit 48, a decoder 50, a receiving part 52 of the previously mentioned USART, the loop-back control 38 and the data communications interface 40. The encoder 34 and decoder 50 define a codec and are on integrated circuits (IC) identified hereinafter. Likewise, the transmitting part 36 and receiving part 52 of the USART are on a single USART IC.

Figure 2:
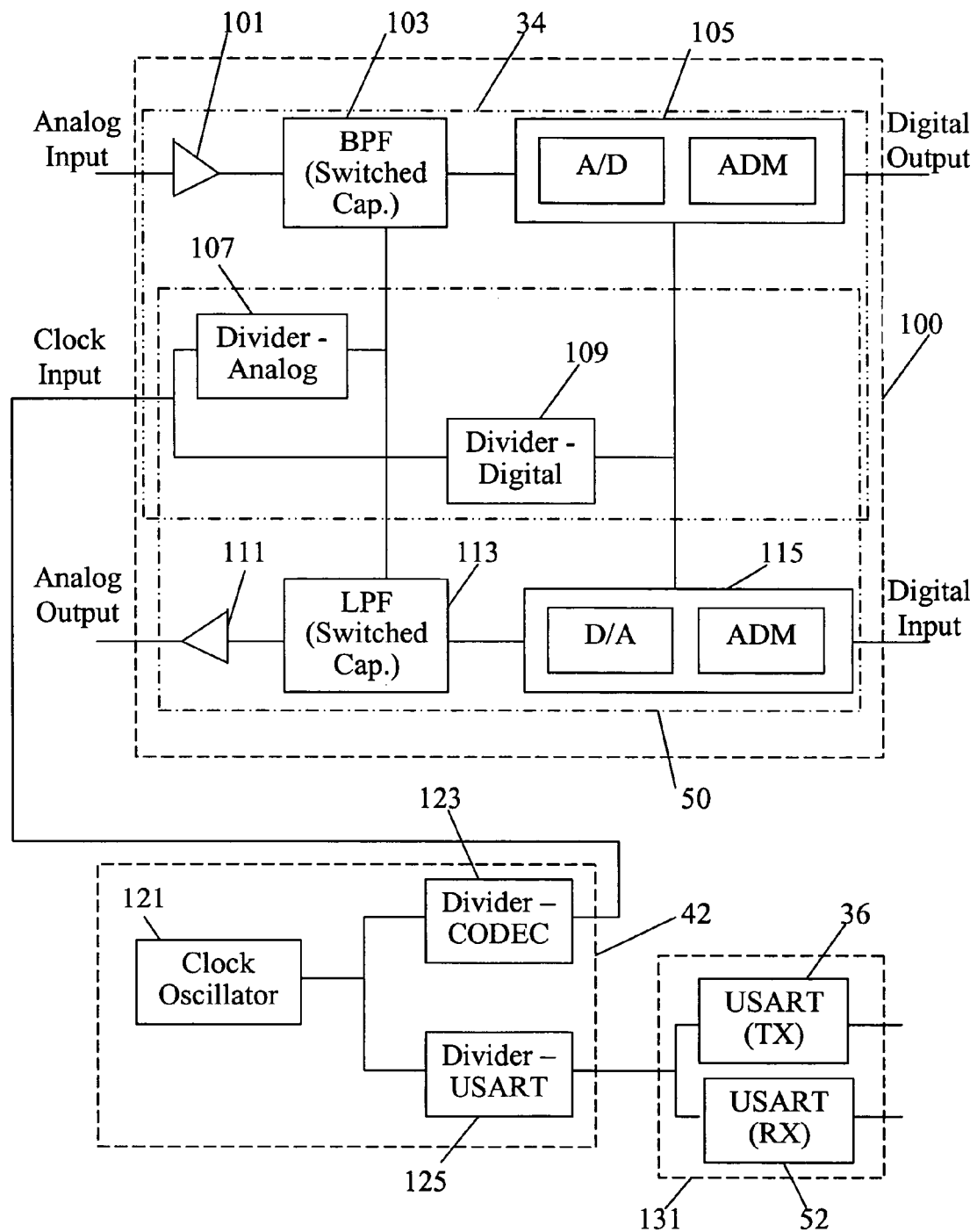
FIG. 2 is a block diagram of the codec and the clock system used in the embodiment of FIG. 1.

In FIG. 2 the encoder 34, decoder 50 and clocking system 42 of FIG. 1 are shown in more detail. With reference to FIG. 2, a codec IC 100 includes the encoder 34 and the decoder 50. Encoder 34 includes an amplifier 101, a band pass filter 103, ADM encoding 105, and two clock signals derived from a single clock. The clock for the switched capacitor band pass filter 103 is provided through divider—analog 107. The clock for the ADM encoding 105 is provided through divider—digital 109. The low pass and high pass cut-off frequencies for the switched capacitor band pass filter 103 are determined by the frequency of the clock from divider—analog 107. The data rate of the signal at the digital output is determined by frequency of the clock from divider—digital 109.

Decoder 50 includes ADM encoding 115, low pass filter 113, amplifier 111 and the clock signals from divider—analog 107 and divider—digital 109. The low pass cut-off frequency for the switched capacitor low pass filter 113 is determined by the frequency of the clock from divider—analog 107. The data rate of the signal expected from the digital input is determined by frequency of the clock from divider—digital 109.

The clock for codec 100 comes from the clocking system 42. A single clock oscillator 121 is divided by divider—codec 123 and divider—USART 125. The output of divider—codec 123 feeds the codec IC 100. The output of divider—USART 125 feeds the USART IC 131.

Referring back to FIG. 1, the chest piece assembly 18 includes a chest piece (not depicted) and a built-in microphone (not depicted). An acoustic signal received from a patient via a chest piece is converted to an analog electrical signal (hereinafter referred to as the "first analog auscultation signal") by the microphone. The chest piece assembly 18 is removably (detachably) plugged into the local transmitting section 20. Although the remote transmitting section (not depicted) also provides for a chest piece assembly to be plugged therein, the chest piece assembly 18 is only needed where the patient is located, i.e., with the local transmitting section 20. The chest piece assembly 18 is plugged into the amplifier 28 of the local transmitting section 20. The chest piece detector 30 of the local transmitting section 20 senses the presence of the chest piece assembly 18 and puts the local stethoscope unit 12 into the transmit mode. In transmit mode the signal is looped back by the loop-back control 38 to the local receiving section 22 and a transmit mode LED (not depicted) is illuminated at the local stethoscope 12. The presence of a chest piece assembly puts the local stethoscope unit 12 into its transmit mode and the absence of the chest piece assembly 18 at the remote stethoscope unit 14 puts the unit 14 into its receive mode.

In the local stethoscope 12, the first analog auscultation signal from the chest piece assembly 18 is fed to the input amplifier 28 where it is amplified. The amplified signal is fed to the encoder 34 through two paths, one direct via a line 54 and one through the first low frequency boost circuit 32. The first low frequency boost circuit amplifies a portion of the first analog auscultation signal having frequencies lower than a predetermined frequency level so as to generate a boosted segment signal. The two signals, the first analog auscultation signal and the boosted segment signal, are electrically combined at the input of the encoder 34. The encoder 34 provides filtering, analog to digital (A/D) conversion, and, in the preferred embodiment, AMD/CVSD encoding. ADM stands for adaptive delta modulation. The best known specific implementation of ADM is continuously variable slope delta (CVSD) modulation. Although AMD/CVSD encoding is the preferred coding, and has not been used in the prior art in a stethoscope system, it is contemplated that other encoding schemes may be used with the present invention, such as PCM, ADPCM, and a generic ADM, all of which are described in the Background Section. With each encoding scheme, some degree of compression is involved.

In the preferred embodiment, the encoder 34 and decoder 50 are provided by an ADM/CVSD codec available from commercial IC manufacturers. In its intended application, the internal filter of the ADM/CVSD encoder of these ICs is a bandpass filter with a nominal low frequency cut-off of approximately 300 Hz and a nominal high frequency cut-off that can vary. With most codec ICs (including the ICs used in the preferred embodiment), the nominal high frequency cut-off is approximately 3,400 Hz. In the preferred embodiment, the ADM/CVSD codec IC was selected wherein this filter is implemented using the switched capacitor technique. To shift this pass band to the desired frequency band of the first analog auscultation signal, the clock from the clocking system 42 driving the ADM/CVSD IC containing the encoder 34 and decoder 50 is reduced (scaled down) by a factor in the nominal range of 4 to 6. This scaling down of the clock has the effect of shifting the bandpass filter's low frequency cut-off to the range of 75 Hz–50 Hz, and the high frequency cut-off to the range of 825 Hz–550 Hz. In other words, the frequency at which the capacitors of a switched capacitor filter are switched determines certain frequency characteristics of the filter. Hence, the cut-off frequency of the filter can be shifted up or down by adjusting the capacitor switching frequency up or down. Thus, if the clock to a switched capacitor filter with a pass band of 300 Hz to 3,400 Hz is scaled down by a factor of five, the filter would then have a pass band of 60 Hz to 667 Hz. The first embodiment of the present invention allows for a broad range of scaling factors. The exact choice will depend upon the specific requirements of a given implementation.

As indicated above, the encoder 34 has a cut-off frequency representing a frequency at which the first analog auscultation signal attenuation becomes significant. This is not an abrupt frequency cut-off, but specifies a point within the frequency roll-off. Likewise, the microphone of the chest piece assembly 18 attenuates the lower frequencies of the audio signal. The first low frequency boost circuit 32 amplifies the portion of the first analog auscultation signal approximately falling below cut-off frequency of the encoder 34 (the "predetermined frequency level") to correspondingly compensate for the frequency roll-off. In other words, the first low frequency boost circuit boosts the amplitudes the boosted signal segment, and this boosted signal segment preferably starts approximately at the cut-off frequency of the encoder 34, although starting at lower frequencies below the cut-off frequency would still be of assistance. The boosted signal segment may also compensate for a microphone that has a cut-off frequency higher than the desired low frequency response.

After passing through the internal filter of the encoder 34, the first analog auscultation signal is converted to a digital signal by the internal A/D converter of the encoder 34. The digitized signal is put through the ADM/CVSD algorithm and then delivered as the digital output signal from the encoder 34. CVSD encoding is a specific form of ADM and while it is the preferred embodiment, other forms of ADM also may be used with the present invention, along with PCM and ADPCM.

The output of the encoder 34 is a compressed digital signal (hereinafter, the "digital auscultation signal") which goes to the transmitting part 36 of the USART. The USART is a flexible IC which can be configured to produce an asynchronous bit stream if the desired data communications channel 16 is to be asynchronous or a synchronous bit stream if the desired communication channel 16 is to be synchronous. The output of the USART goes to the RS232 data communications interface 40 and the output of the RS232 interface 40 is cabled to the data communications channel 16, which delivers the signal to the RS232 interface 40 at the receiving section 22 of the remote unit 14.

In the local transmitting section 22 of the local stethoscope unit 12 with the chest piece assembly 18 plugged in, the unit 12 is in its transmit mode and the signal from the encoder 34 is also looped back via the loop-back control 38 to the decoder 50. The analog output of the decoder 50 goes to two paths—one to the circuitry (low pass filter 46 and second low frequency boost circuit 48) for the bell position of the bell/diaphragm toggle switch 44 and one for the diaphragm side of the switch 44. When the switch 44 is in the diaphragm position (switched to the diaphragm input terminal), the analog signal is fed directly to the headset driver 24, which provides the auscultation sounds to the headset 26 for the person at the patients location monitoring the auscultation exam to hear. When the switch is in the bell position (switched to the bell input terminal), the analog signal is fed to both the low pass filter 46 and the second low frequency boost circuit 48. The low pass filter 48 blocks higher frequency sounds such as lung sounds so that the listener can concentrate on the lower frequency heart sounds. In the preferred embodiment, the cut-off frequency for the low pass filter is nominally set at 250 Hz although the present invention allows for any cut-off frequency up to the cut-off frequency of the internal filters of the ADM/CVSD codec. The second low frequency boost circuit 48 provides compensation boost for the frequencies that fall below the cut-off frequency of the ADM/CVSD codec and cover down to nominally 20 Hz, although the present invention allows for other lower limits for the second low frequency boost circuit 48. The output from the low pass filter 46 and the second low frequency boost circuit 48 are electrically combined at the headset driver 24, which drives the headset 26 for the person monitoring the auscultation exam to hear the auscultation sounds.

When the local stethoscope unit 12 is in its transmit mode, the signal loop back can optionally occur from the transmitting part of the USART 36 to the receiving part of the USART 52, or from the output of the input amplifier 28 to the low pass filter 46, second low frequency boost circuit 48, and the headset driver 24.

At the remote stethoscope unit 14, the digital auscultation signal goes to the receiving part 40 of the USART, which is configured to match the mode of the communications channel 16 and the local stethoscope transmit part 36 of the USART. The signal then goes to the decoder 50 in the remote stethoscope 14. The decoder 50 provides the reverse ADM/CVSD algorithm, digital to analog conversion and a band pass filter similar to the one in the encoding path. The same ADM algorithms used in the local stethoscope 12 are used in the remote stethoscope 14. The scaling of the clock frequency affects the ADM/CVSD decoder path filter the same as the filter in the ADM/CVSD encoder path. The analog signal generated by the decoder 50 of the remote stethoscope unit 14 is referred to as the "regenerated auscultation signal").

Just as described with the local stethoscope 12, the analog output of the decoder 50 (regenerated auscultation signal) goes to two paths—one to the circuitry for the bell position of the bell/diaphragm toggle switch 44 and one for the diaphragm side of the switch 44. When the switch 44 is in the diaphragm position, the analog signal is fed directly to the headset driver 24, which provides the auscultation sounds to the headset 26 for the listener to hear at the clinician's location. When the switch 44 is in the bell position, the analog signal is fed to both the low pass filter 46 and the second low frequency boost circuit 48. The low pass filter 46 blocks higher frequency sounds such as lung sounds so that the clinician can concentrate on the lower frequency heart sounds. In the preferred embodiment, the cut-off frequency for the low pass filter is nominally set at 250 Hz, although the present invention allows for any cut-off frequency up to the cut-off frequency of the internal filters of the ADM/CVSD codec. The second low frequency boost circuit 48 provides compensation boost for the frequencies that fall below the cut-off frequency of the ADM/CVSD codec and cover down to nominally 20 Hz, although the present invention allows for other lower limits for the second low frequency boost circuit 48. The output from the low pass filter 46 and the second low frequency boost circuit 48 are electrically combined at the headset driver 24 of the remote stethoscope 14, which drives the headset 26 for the remote clinician to listen to the auscultation sounds. Hence, with the exception of the source of the operation of the receiving sections 22 of the local and remote stethoscope units 12 and 14 are the same.

With reference to FIGS. 1 and 2, a common clock source of the clocking system 42 is used which allows a synchronization linkage between the data rate and the line interface rate of the communication channel 16. The frequency of the source clock is selected, among other implementation specific requirements, so that the data rate to the USART (36 and 52) and the data line interface rate of the data communications channel 16 may be derived by dividing down the source clock. In the preferred embodiment for an asynchronous communications channel 16, the data rate to the USART would be 7,680 bits per second (b/s) and the line data rate would be 9,600 b/s. The exact frequency of the source clock is further dependent on the codec 100 selected and other circuit implementation specifics.

The embodiment of the present invention provides the following advantages. In the preferred embodiment, the stethoscope units 12 and 14 employ one of several possible low cost communications ADM/CVSD codec ICs for the encoder 34 and decoder 50, which was designed to provide filtering, A/D and D/A conversion and coder/decoder conversion for high quality encoding and decoding of audio in the nominal frequency range of ~300 Hz–3400 Hz. In the preferred embodiment this codec IC is adapted to accommodate the core auscultation frequency range of at least 20 Hz–700 Hz. This adaptation is accomplished by: 1) scaling the operating frequency of the codec IC and internal filters and 2) compensating for any remaining low frequency response shortcomings via the first and second low frequency boost circuits 32 and 48.

With the use of ADM/CVSD encoding, instead of the prior art use of PCM and ADPCM, bandwidth for the first analog auscultation signal is substantially improved. More specifically, when the data communications channel 16 comprises a narrowband telephone line, the prior art designs only provided for an application of an auscultation bandwidth of 30–500 Hz, but in the preferred embodiment of the present invention, the auscultation bandwidth is expanded to 20–700 Hz. Consequently, a patient's auscultation sounds at one location may be transmitted, in real time using a low bit rate, to a clinician at another location with a greater bandwidth for the auscultation signal. The bit rate is sufficient low that a normal telephone line can be used as part of the data communications system.

However, it should be appreciated that aspects of the preferred embodiment of the stethoscope system 10 may be used with data communications channels 16 other than a narrow bandwidth telephone line where a low bit rate is critical. The data communications channel 16 may include a modem, an IP (internet protocol) network, a direct cable connection, wireless or any communications means to interconnect the local and remote stethoscope units 12 and 14. As one example of one bandwidth limited application, telemedicine involves video conferencing with a medical application. Typically, the single transmission line carries voice, video, control and a (user) data channel multiplexed together. The video conferencing standards (H.324 for POTS, H.320 for ISDN and H.323 for IP) include all those channels and the multiplexing. Audio, video and control have to go across the same transmission line as the auscultation data.

Low frequency compensation is needed regardless of the type of encoding used in the codec (encoder 34 and decoder 50), i.e., regardless of whether the encoding is that ADM-CVSD (as used in the preferred embodiment), PCM, ADPCM or generic ADM. In the preferred embodiment, the low frequency compensation can be accomplished in the transmitting section 20 of the local stethoscope unit 12 and also in the receiving sections 22 of the local and remote stethoscope units 12 and 14. Although not preferable, it is contemplated that low frequency compensation may be undertaken only in the transmitting section 20 and not in the receiving sections 22. Since the frequency roll-off is slow rather than abrupt for the codec, having only one boost circuit 48 at the receiving section 20 still has value, although limited, because background noise is amplified along with the desired signal and the signal-to-noise (S/N) ratio suffers. Having the boost circuit 32 only at the transmitting section has much more value because the S/N ratio is better. Having the boost circuits at both ends (first and second low frequency boost circuits 32 and 48) is optimal, because the S/N ratio is preserved. Additionally, this allows for the user to be provided with a selectable option for further boosting the low end (along with knocking down the higher frequencies) to allow the user to concentrate on the low frequency heart sounds. The very low frequency boost is intended to compensate for the codec internal filter as well as the microphone of the chest piece assembly 18 not going low enough in their frequency response. It should be noted that in the preferred embodiment, having half of the boost in the transmitting section 20 partially compensates for the codec internal filter in both the bell and diaphragm modes and having the other half of the boost in the receiving section 22 compensates in the bell mode only.

Also, in an alternative embodiment, the bi-directional capability of the data communications channel 16 may be used so that a signal may be sent from the remote stethoscope unit 14 to the local stethoscope unit to switch in the second low frequency boost circuit 48 when the remote stethoscope unit 14 goes into bell mode and switch out the second low frequency boost circuit 48 when the remote stethoscope unit 14 goes out of the bell mode and into the diaphragm mode. The frequency compensating can be further employed to boost the very low frequency components to enhance the heart sounds against the higher frequency sounds, similar to the Bell side of a typical acoustic stethoscope.

While not illustrated in the preferred embodiment, it is contemplated that the present invention may include variations in how the second low frequency boost 48 is applied. By sending a command from the remote stethoscope 14 to the local stethoscope 12, the second low frequency boost circuit 50 can be enabled or disabled under control of the clinician at the remote stethoscope 14. This could be used to provide greater difference in the amount of second low frequency boost between the bell and diaphragm operation.

The stethoscope system 10 eliminates the need for a data buffer to handle data over-runs by maximizing the data speed for the specific line rate. For example, if the RS232 interface 40 of the remote receiving section 22 is connected to a personal computer (PC) with its COM port set to 9.6 Kb/s and the maximum line data of 9.6 Kb/s is being transmitted over an asynchronous communications channel 16 (7.68 Kb/s data rate), then it would be impossible for the PC to deliver too much data. Should there be a momentary stall of the data on the data communications channel, the present invention allows for a data buffer to be used at the receiving sections 22.

The selection of the clock frequency to the ADM/CVSD IC not only scales the filters, but is also affect the coding operation and the output data rate and input data rate. In addition to selecting the clock frequency to satisfy filter scaling requirements, the preferred embodiment of the present invention may select the ADM/CVSD IC clock frequency to satisfy specific data rate requirements. The clock can be selected to produce a 9.6 Kb/s data output for the IC to the USART for 9.6 Kb/s synchronous data communications channel operation. For asynchronous data communications channel operation, for every eight data bits to the USART there is a Start bit and a Stop bit for a total of ten bits at the 9.6 Kb/s data channel interface. Thus a 7.68 Kb/s data stream would result in a 9.6 Kb/s data interface line speed. In this configuration, the ADM/CVSD IC clock would be selected to produce a data rate of 7.68 Kb/s.

When ADM/CVSD is used in the encoder 34 and decoder 50, the self-synchronizing of the encoding and decoding eliminates the need for any synchronization or framing patterns at the data communications channel interface 16. The self-sync feature is a characteristic of ADM/CVSD which produces only one bit for each algorithmic assessment. In synchronous mode with a synchronous data communications channel interface 16, the data rate can be equal to the line speed. In asynchronous mode with an asynchronous data communications channel interface 16, the data speed may be generated by having a special system clock frequency to match the low speed asynchronous data interface line rate of 9,600 b/s so as to the maximum data rate of 7,680 b/s handled by that line.

In the preferred embodiment, the same stethoscope unit may be used as the local stethoscope unit 12 and remote stethoscope unit 14. When a chest piece assembly 18 is plugged into the stethoscope unit (therefore, making it the local stethoscope unit 12 where the patient is located), its presence is sensed and the unit 12 automatically goes into its transmit mode. In transmit mode, the auscultation signal is sent out the communications interface to the remote stethoscope 14 and also is looped back to the receiving section 20 of the local stethoscope unit 12 so that a clinician with the patient (or the patient) may also hear the same sounds as the clinician with the remote stethoscope 14 at the remote location. In alternative embodiments, the auscultation signal loop back may occur optionally from the analog output of the chest piece assembly 18 (before or after the first low frequency boost circuit 32) to the receiving section 22 (before or after the second low frequency boost circuit 48), or from the digital output of the ADM/CVSD codec to the digital input of the codec, or from the output of the USART to the input of the USART. If the chest piece assembly is not plugged in, the unit automatically goes into its receive mode (therefore referred to as the "remote stethoscope unit 14").

Although specific embodiments have been illustrated and described herein, it will be appreciated by those of ordinary skill in the art that any arrangement which is calculated to achieve the same purpose may be substituted for the specific embodiment shown. This application is intended to cover any adaptations or variations of the present invention. Therefore, it is manifestly intended that this invention be limited only by the claims and the equivalents thereof.

What is claimed is:

1. A stethoscope system, comprising:
   a local stethoscope unit including a chest piece assembly to generate a first analog auscultation signal and a local transmitting section to receive the first analog auscultation signal;
   the local transmitting section including a first low frequency boost circuit coupled to the chest piece assembly and capable of amplifying a portion of the first analog auscultation signal having frequencies lower than a predetermined frequency level to generate a boosted segment signal, a local encoder coupled to the chest piece assembly and to the first low frequency boost circuit and responsive to the first analog auscultation signal and the boosted segment signal to generate a compressed digital auscultation signal;
   a data communications channel coupled to the local encoder to receive the digital auscultation signal; and
   a remote stethoscope unit including a remote receiving section and a remote headset, the remote receiving section being coupled to the data communications channel and responsive to the digital auscultation signal to generate a second analog auscultation signal for the remote headset.

2. The stethoscope system according to claim 1, wherein the local encoder has a cut-off frequency and the predetermined frequency level is approximately equal to the cut-off frequency.

3. The stethoscope system according to claim 1, wherein the local stethoscope unit further includes a local headset and a local receiving section; the local receiving section includes a local decoder coupled to the local encoder and responsive to the digital auscultation signal to generate a third analog auscultation signal; and the local receiving section further includes a second low frequency boost circuit and a low pass filter both coupled between the local decoder and the headset.

4. The stethoscope system according to claim 3, wherein the local receiving section further includes a switch having an output coupled to the local headset and being operable to select an input from a diaphragm input terminal or a bell input terminal; the second low frequency boost circuit and low pass filter both being coupled between the bell input terminal and the output of the local decoder; and the output of local decoder being coupled to the diaphragm input terminal.

5. The stethoscope system according to claim 4, wherein the remote stethoscope unit further includes a remote transmitting section coupled to the local receiving section through the data communications channel and being capable of generating a switching signal to control the selection by the switch of either the diaphragm input terminal or the bell input terminal.

6. The stethoscope system according to claim 1, wherein the remote receiving section includes a second low frequency boost circuit and a low pass filter both having the second analog auscultation signal as their input and both having their output coupled to the remote headset.

7. The stethoscope system according to claim 6, wherein the remote receiving section further includes a remote decoder coupled to the data communications channel and responsive to the digital auscultation signal to generate the second analog auscultation signal; a switch having an output coupled to the remote headset and being disposed in switching relationship with a diaphragm input terminal and a bell input terminal; the second low frequency boost circuit and the low pass filter both being coupled between the bell input terminal and the output of the remote decoder; and the output of remote decoder further being coupled to the diaphragm input terminal.

8. The stethoscope system according to claim 1, wherein the local encoder comprises a codec integrated circuit, with the codec integrated circuit having a first operating frequency range and including scaling means for scaling down the first operating frequency range to provide a second frequency range having a low frequency at least as low as 75 Hz and a high frequency at least as high as 550 Hz.

9. The stethoscope system according to claim 1, wherein the data communications channel is a bandwidth-limited telephone line and the local encoder is an adaptive delta modulation (ADM) and continuously variable slope delta (CVSD) modulation encoder.

10. The stethoscope system according to claim 9, wherein the local transmitting section further includes a local data communications interface coupled between the local encoder and the data communications channel and operable to provide the digital auscultation signal to the data communications channel and the remote receiving section includes a remote data communications interface coupled to the data communications channel to receive the digital auscultation signal, the local and remote data communications interfaces being selectively synchronous or asynchronous.

11. The stethoscope system according to claim 10, wherein the local transmitting section includes a clock system having a clock source and a clock divider coupled to the clock source to generate a line rate clock and a data rate clock; the data communications interface comprising an asynchronous data communications channel interface; and the local transmitting section has a low speed asynchronous line interface rate of 9,600 bits per second driven by the line rate clock and a data rate of 7,680 bits per second driven by the data rate clock.

12. The stethoscope system according to claim 10, wherein the data communications interface includes a synchronous data communications channel interface with a data rate of the digital auscultation signal being equal to a line rate.

13. The stethoscope system according to claim 1, wherein the local stethoscope unit further includes a local receiving section, with the local stethoscope unit having a local transmit mode and a local receive mode; the remote stethoscope unit further including a remote transmitting section, with the remote stethoscope unit having a remote transmit mode and a remote receive mode; the chest piece assembly being detachably coupled to the local transmitting section; the local stethoscope unit being configured to operate in the local transmit mode and the remote stethoscope unit being configured to operate in the remote receive mode in response the chest piece assembly being coupled to the local transmitting section and not coupled the remote transmitting section.

14. A stethoscope unit, comprising:
a chest piece assembly to generate a first analog auscultation signal and a transmitting section to receive the first analog auscultation signal; and
the transmitting section including a first low frequency boost circuit coupled to the chest piece assembly capable of amplifying a portion of the first analog auscultation signal having frequencies lower than a predetermined frequency level to generate a boosted segment signal, an encoder coupled to the chest piece assembly and to the first low frequency boost circuit and responsive to the first analog auscultation signal and the boosted segment signal to generate a compressed digital auscultation signal.

15. The stethoscope unit according to claim 14, further including a headset and a receiving section; the receiving section further includes a decoder coupled to the encoder and responsive to the digital auscultation signal to generate a second analog auscultation signal; and the receiving section includes a second low frequency boost circuit and a low pass filter both coupled between the decoder and the headset.

16. The stethoscope system according to claim 15, wherein the receiving section further includes a switch having an output coupled to the headset and being operable to select an input from a diaphragm input terminal or a bell input terminal; the second low frequency boost circuit and low pass filter both being coupled between the bell input terminal and the output of the decoder; and the output of the decoder being coupled to the diaphragm input terminal.

17. The stethoscope system according to claim 16, wherein the encoder comprises a codec integrated circuit, with the codec integrated circuit having a first operating frequency range and including scaling means for scaling down the first operating frequency range to provide a second frequency range having a low frequency at least as low as 75 Hz and a high frequency at least as high as 550 Hz.

18. The stethoscope system according to claim 17, wherein the encoder is an adaptive delta modulation (ADM) and continuously variable slope delta (CVSD) modulation encoder.

19. The stethoscope system according to claim 18, wherein the transmitting section includes an asynchronous data communications interface coupled to the encoder and a clock system having a clock source and a clock divider coupled to the clock source to generate a line rate clock and a data rate clock and wherein the transmitting section has a low speed asynchronous line interface rate of 9,600 bits per second driven by the line rate clock and a data rate of 7,680 bits per second driven by the data rate clock.

20. The stethoscope system according to claim 18, wherein the local transmitting section includes a synchronous data communications interface coupled between the encoder with a data rate of the digital auscultation signal being equal to a line rate.

21. A stethoscope system, comprising:
a local stethoscope unit including a local transmitting section and a local receiving section, with the local stethoscope unit having a local transmit mode and a local receive mode;
a remote stethoscope unit including a remote transmitting section and a remote receiving section, with the remote stethoscope unit having a remote transmit mode and a remote receive mode;
a local chest piece assembly detachably coupled to the local transmitting section to generate an analog auscultation signal;
a remote chest piece assembly detachably coupled to the remote transmitting section to generate an analog auscultation signal;
wherein, the local stethoscope unit is configured to operate in the local transmit mode when the local chest piece assembly is coupled to the local transmitting section of the local stethoscope, and the remote chest piece assembly is not coupled to the remote transmitting section of the remote stethoscope;
and wherein the remote stethoscope unit is configured to operate in the remote receive mode when the local chest piece assembly is coupled to the local transmitting section of the local stethoscope and the remote chest piece assembly is not coupled to the remote transmitting section of the remote stethoscope;
the local transmitting section in the transmit mode being coupled to the remote receiving section and the chest piece assembly and being responsive to the analog auscultation signal to generate and transmit a digital auscultation signal to the remote receiving section;

the remote receiving section in the receive mode being responsive to the transmitted digital auscultation signal to regenerate the analog auscultation signal; and a remote headset to receive the regenerated analog auscultation signal.

22. The stethoscope system according to claim 21, wherein the local stethoscope unit further includes a local headset coupled to the local receiving section to receive the digital auscultation signal.

23. The stethoscope system according to claim 21, wherein the local stethoscope unit further includes a local headset coupled to the local chest piece assembly to receive the analog auscultation sound.

24. The stethoscope system according to claim 23, wherein the remote transmitting section, remote receiving section, and remote headset and the local transmitting section, local receiving section and local headset respectively are identical in design.

25. The stethoscope system according to claim 21, wherein the local transmitting section is coupled to the remote receiving section by way of a data communications channel.

26. The stethoscope system according to claim 21, wherein the local and remote transmitting section each include a chest piece detector to automatically trigger the transmit mode in response to detecting the presence of the local or remote chest piece assembly respectively and to automatically trigger the receive mode in response to not detecting the presence of the local or remote chest piece respectively assembly.

* * * * *